United States Patent [19]

Bilstad et al.

[11] Patent Number: 4,610,781
[45] Date of Patent: Sep. 9, 1986

[54] FLUID PROCESSING SYSTEM WITH FLOW CONTROL MANIFOLD

[75] Inventors: Arnold C. Bilstad, Deerfield; Robert J. Kruger, Arlington Heights, both of Ill.

[73] Assignee: Baxter Travenol Laboratories, Inc., Deerfield, Ill.

[21] Appl. No.: 567,363

[22] Filed: Dec. 30, 1983

[51] Int. Cl.$^4$ ............................................. B01D 13/00
[52] U.S. Cl. ..................................... 210/85; 210/96.2; 210/321.3; 210/433.2
[58] Field of Search ................... 210/96.2, 929, 433.2, 210/927, 321.1, 321.2, 321.3, 85; 604/4, 6; 137/266

[56] References Cited

U.S. PATENT DOCUMENTS

| | | | |
|---|---|---|---|
| 2,954,028 | 9/1960 | Smith | 137/266 X |
| 3,328,255 | 6/1967 | Ilg | 604/4 X |
| 3,359,910 | 12/1967 | Latham | 103/6 |
| 3,402,853 | 9/1968 | Perl | 251/9 X |
| 3,405,706 | 10/1968 | Cinqualbre | 128/2 |
| 3,411,534 | 11/1968 | Rose | 604/32 X |
| 3,438,551 | 4/1969 | Belisle | 222/182 |
| 3,545,671 | 12/1970 | Ross | 604/34 |
| 3,550,619 | 12/1970 | Halasz | 251/7 X |
| 3,634,228 | 1/1972 | Latham, Jr. | 210/636 |
| 3,679,331 | 7/1972 | Kushner | 222/214 X |
| 3,722,502 | 3/1973 | Besuner et al. | 128/2 |
| 3,774,762 | 11/1973 | Lichtenstein | 210/96.2 X |
| 3,782,382 | 1/1974 | Naftulin et al. | 128/2 |
| 3,985,134 | 10/1976 | Lissot et al. | 128/214 R |
| 4,058,363 | 11/1977 | Silbert | 210/927 |
| 4,061,142 | 12/1977 | Tuttle | 604/34 |
| 4,181,121 | 1/1980 | Schwoboda et al. | 128/762 |
| 4,185,629 | 1/1980 | Cullis et al. | 604/6 |
| 4,206,767 | 6/1980 | Wingrove | 604/34 |
| 4,370,983 | 2/1983 | Lichtenstein | 210/929 X |
| 4,416,778 | 11/1983 | Rogers | 222/214 |

Primary Examiner—Frank Spear
Attorney, Agent, or Firm—Paul C. Flattery; Bradford R. L. Price; Eugene M. Cummings

[57] ABSTRACT

A fluid processing system includes an integral flow control and distribution manifold for establishing fluid communication between conduit segments of the system. In use, the fluid manifold is received in an actuator head of an associated processor apparatus, wherein valving elements selectively crimp valving passageways in the manifold to perform the procedure. The fluid circuit of the system accommodates multiple procedures, obviating the need to stock multiple systems and enabling manufacturing economics to be realized from higher production volumes.

7 Claims, 17 Drawing Figures

FIG. 16 (CONTINUOUS FLOW)

FIG. 17 (PARTIAL RECIRCULATION)

FLUID PROCESSING SYSTEM WITH FLOW CONTROL MANIFOLD

BACKGROUND OF THE INVENTION

The present invention relates generally to fluid processing systems and apparatus, and more particularly to a disposable fluid processing system incorporating an integral distribution manifold which provides for more economical construction and more convenient installation, and an apparatus for use therewith.

Various methods and apparatus have been developed which utilize disposable single-use processing systems formed of plastics such as vinyl for accomplishing fluid processing procedures. In the medical field, for example, processing systems have been developed for blood fractionation procedures, such as plasmapheresis, leukopheresis and plateletpheresis, wherein whole blood is separated into one or more fractions by means of either a filter element or by means of centrifugration, and for hemodialysis procedures, wherein diffusion exchange occurs through a membrane between whole blood and a dialysis solution.

Typically, such disposable processing systems are relatively complex in construction, requiring a plurality of Y-type and T-type connections and associated solvent bonds to establish necessary fluid flow paths between the system components. This complexity not only adds to the cost of manufacture, but also works to the detriment of system reliablity. Accordingly, it is desirable in disposable fluid processing systems that the number of connections be minimized to the extent possible. The present invention is directed to a flow system and actuator apparatus for use therewith wherein the majority of fluid connections are made along a single seal line forming part of a common fluid flow control and distribution manifold.

It is also desirable, to further reduce manufacturing cost, that a single flow system construction have the capability of performing multiple fluid processing procedures. In particular, in blood processing applications it is desirable that a single system construction serve for both batch flow procedures, wherein an aliquot of blood is first drawn from a donor and processed during a recurring draw cycle, and is then returned to the donor during recurrent intervening return cycles; and for continuous flow procedures, wherein blood is continuously drawn, processed, and returned, using either two separate phlebotomy needles or a single dual lumen needle. This permits larger quantities of a single flow system construction to be manufactured, with attendant reductions in material and labor costs. The present invention is directed to a flow system and apparatus which accommodates these procedures without modification, thereby realizing the benefits of higher volume production.

Furthermore, the processor apparatus with which disposable processing systems are used typically include multiple pump, detector and valving elements on which particular components and tubing segments of the fluid circuit must be individually installed. Consequently, the set-up procedure may be undesirably complex so as to require a specially trained operator, and may require an undesirably long time period to complete. Even with the use of a specially trained operator, the potential remains for error, as where the wrong tubing segment is installed on a particular element of the apparatus. Accordingly, it is desirable that the procedure for installing a flow system in an apparatus be as simple as possible, preferably establishing operative connections to critical valving and other elements of the apparatus with insertion of a single system component, and with minimal opportunity for error. The present invention is directed to a disposable flow system and apparatus wherein the system includes a fluid distribution manifold which is received as a unit in the apparatus to establish with one insertion step operative connection with a plurality of valving elements.

Accordingly, one of the principal objects of the present invention is to provide a new and improved fluid processing system for performing a fluid fractionation procedure, such as hemodialysis or plasmapheresis.

It is another principal object of the present invention to provide a fluid processing system and apparatus which accommodates a number of different fluid fractionation procedures without modification.

It is another principal object of the present invention to provide a fluid processing system and apparatus which is easier to set-up and which provides reduced possibility for operator error.

It is another principal object of the present invention to provide a disposable fluid flow system for use in conjunction with fluid separator or processing apparatus which is more economical to manufacture.

SUMMARY OF THE INVENTION

A fluid flow system for performing a fluid processing procedure includes a pair of fluid-impermeable sheets, and a plurality of tubing segments at least one end portion of which are generally disposed in parallel-spaced relationship in a common plane. The sheets are sealed together about their periphery and along a seal line in the commond plane encompassing the end portions of the tubing to form a liquid-sealed fluid distribution manifold in communication with the tubing segments, whereby the distribution manifold and the tubing segments together form a fluid circuit for the procedure.

The invention is further directed to a fluid system comprising a pair of fluid-impermeable sheets, and fluid sealing means joining the sheets to form a fluid circuit therebetween. The fluid circuit includes manifold inlet port means connected to the manifold at a first location for admitting fluid to the manifold, an outlet port means connected to the manifold at a second location for withdrawing fluid from the manifold, and a fluid processing means connected to the manifold at a third location for processing fluid in the circuit. Pump means urge fluid through at least a portion of the manifold in one direction to admit fluid to the processing means, and urge fluid through the portion of the manifold in the reverse direction to remove fluid from the processing means.

The invention is further directed to processing apparatus for use in conjunction with a fluid flow system of the type having a fluid manifold including a plurality of tubing segments on one side thereof and a plurality of valving passageways along the opposite side thereof. The apparatus includes a receptacle for receiving the valving side of the fluid manifold, and a plurality of valve actuator assemblies disposed in the receptacle for selectively closing the valving passageways. Process control means are included for actuating the valving means to accomplish the fluid processing procedure.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
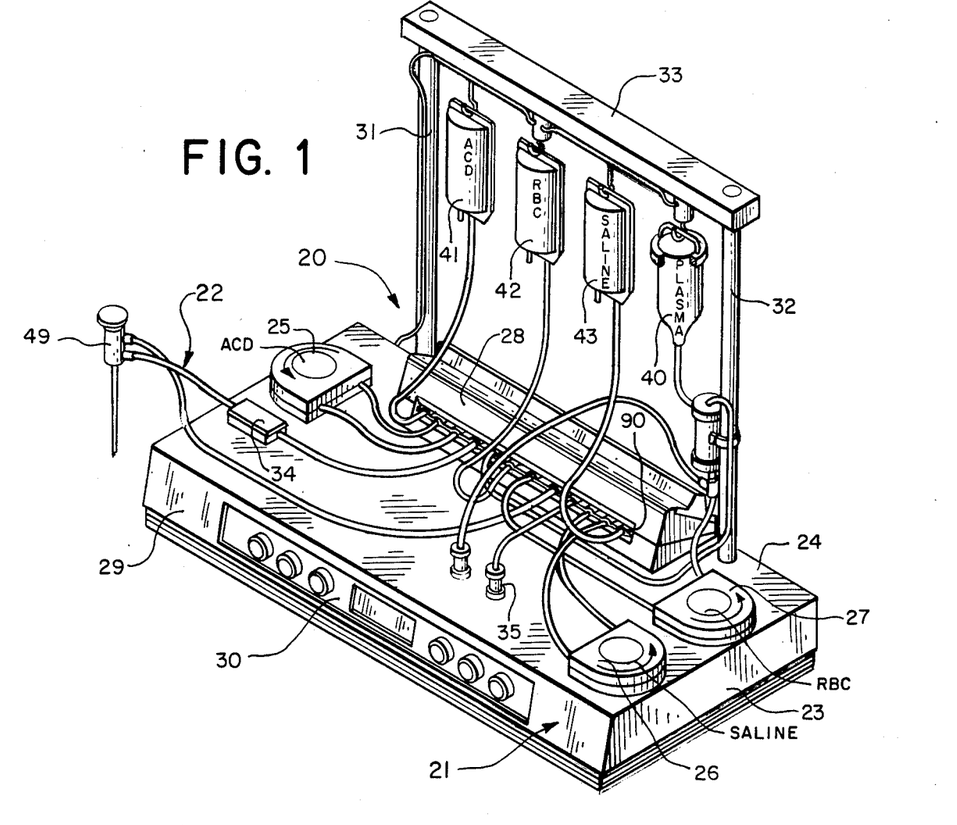
FIG. 1 is a perspective view of a plasmapheresis blood fractionation system and actuator apparatus constructed in accordance with the invention.

Referring to the Figures, and particularly to FIG. 1, a blood fractionation system 20 constructed in accordance with the invention is seen to comprise a processor apparatus 21 and a disposable flow system 22. The apparatus 21 is preferably contained within a housing 23 of flat generally rectangular proportions. On the top surface 24 of the housing the apparatus 21 preferably includes a peristaltic-type anticoagulant (ACD) pump 25, a peristaltic-type saline pump 26 and a peristaltic-type red blood cell (RBC) pump 27. These pumps, which may be conventional in construction and operation, are adapted in a known manner to receive tubing segments included in flow system 22. A control head 28 is provided adjacent the rear edge of surface 24 for operative engagement with flow system 22.

Housing 23 further includes on its front surface 29 a control panel 30 for receiving operator-inputs and for providing indications of various system operating parameters. The housing preferably further includes a pair of vertical support poles 31 and 32 from which a horizontal bar 33 is mounted to allow a plurality of collection and dispensing containers of conventional construction to be hung by means of appropriate hangers.

Figure 2:
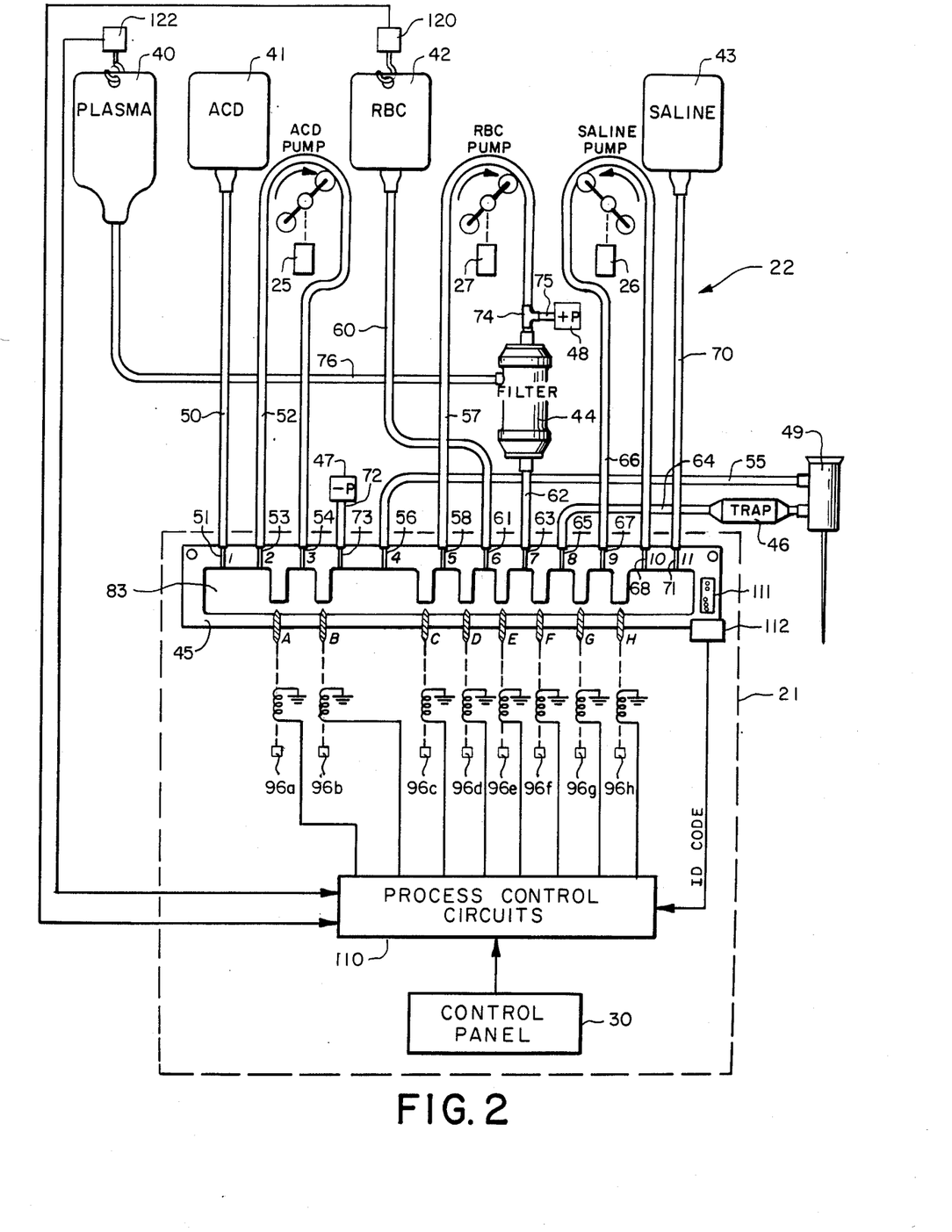
FIG. 2 is a functional block diagram showing the principal components of the blood fractionation system and apparatus of FIG. 1.

The fractionation apparatus 21 operates in conjunction with a disposable fluid circuit, generally identified by the reference numeral 22 in FIG. 1 and shown schematically in FIG. 2. Basically, the fluid circuit 22 is seen to include a plasma container 40 for receiving and storing plasma separated during the procedure, an ACD container 41 for storing a quantity of anticoagulant fluid to be added to derived whole blood, an RBC container 42 for storing a quantity of processed whole blood, and a saline container 43 for storing a quantity of saline solution to be added to the processed whole blood. In addition, the fluid circuit 22 includes a filter element 44 for separating plasma (or another desired blood fraction) from whole blood, and a flow control manifold 45 which, in accordance with the invention, provides necessary fluid interconnections between the system components in accordance with the requirements of the procedure. A bubble trap 46 may be provided to detect the presence of a bubble or other liquid absence in fluid returned to the donor, and a pressure monitor 47 may be provided to sense a negative pressure in the input circuit associated with the collapse of a vein. A positive pressure monitor 48 may be provided in association with the system filter 44 to sense proper conditions for operation of the the filter. When the system is installed, the trap 46 is received within the apparatus fluid absence detector 34. The negative pressure monitor means 47 and positive pressure monitor 48 are advantageously provided on the top panel 24 of the apparatus housing, as shown in FIG. 1.

Depending on the particular procedure in use, the fluid circuit 22 may be utilized in conjunction with a single-lumen phlebotomy needle, a dual-lumen phlebotomy needle or a pair of single lumen phlebotomy needles. In the exemplary embodiment of FIG. 2, the fluid circuit is shown connected to a single single-lumen phlebotomy needle 49. The system may include a conventional needle adaptor assembly to facilitate connection to another type of phlebotomy needle.

Fluid circuit 22 includes a plurlaity of flexible plastic typing segments which form fluid conduits between various components of the fluid circuit. Specifically, the ACD container 41 is connected by a conduit segment 50 to a first fluid port 51 associated with flow control manifold 45. A second tubing segment 52 connects a second fluid port 53 of manifold 45 through ACD pump 25 to a third fluid port 54. A third tubing segment 55 connects a fourth fluid port 56 of manifold 45 to one port of the dual-lumen phlebotomy needle 49. A fourth tubing segment 57 connects a fifth fluid port 58 of the manifold through RBC pump 27 to the inlet port of filter 44.

A fifth tubing segment 60 connects the RBC container 42 to a sixth fluid port 61 of manifold 45. A sixth tubing segment 62 connects a seventh fluid port 63 of manifold 45 to the outlet port of filter 44. A seventh tubing segment 64 connects an eighth fluid port 65 of manifold 45 through trap 46 to the remaining port of the dual-lumen phlebotomy needle 49.

An eighth tubing segment 66 connects a ninth fluid port 67 of manifold 45 through saline pump 26 to a tenth fluid port 68. A ninth tubing segment 70 connects the saline container 43 to an eleventh fluid port 71 of manifold 45. A tenth tubing segment 72 connects a twelfth fluid port 73 of manifold 45 to the negative pressure monitor 47. A T-connector 74 and tubing segment 75 connect the positive pressure monitor 48 to tubing segment 57. A further tubing segment 76 connects the plasma container 40 to the plasma output port of filter 44.

Figure 3:
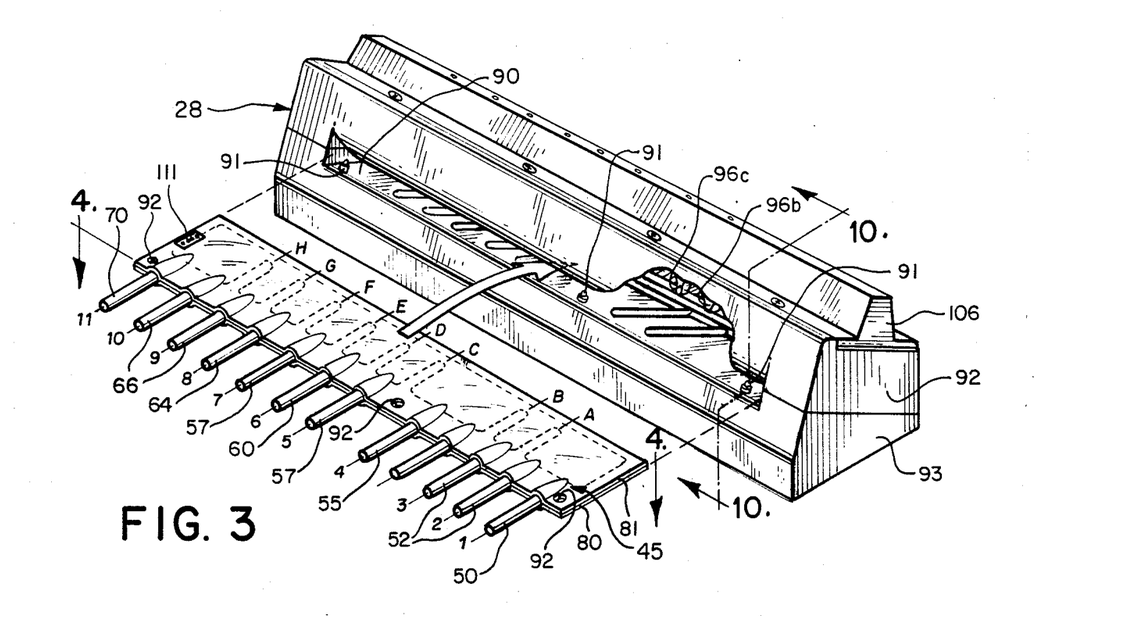
FIG. 3 is an enlarged perspective view of the control head and fluid distribution manifold of the apparatus and flow system of FIG. 1 wherein the actuator head is partially broken away to show the location of valving elements contained therein.
Figure 4:
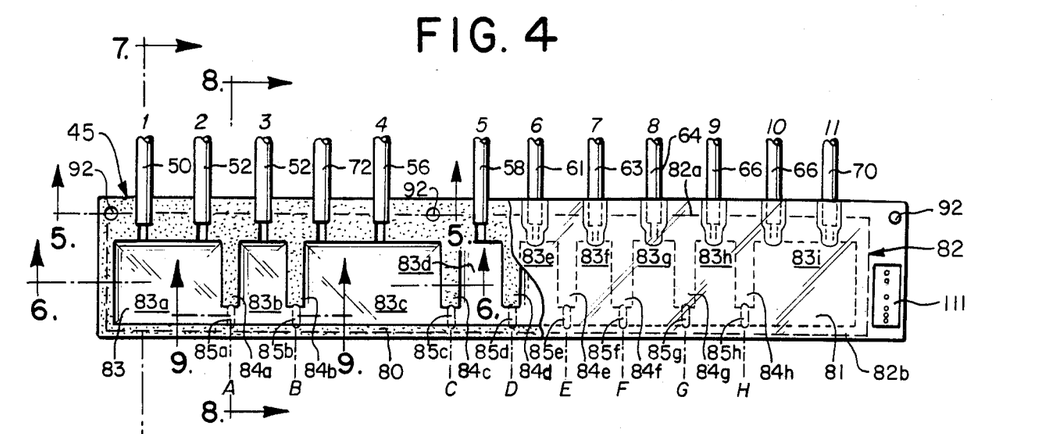
FIG. 4 is an enlarged top elevational view of the fluid distribution manifold of the fluid processing system of FIG. 1 partially in section to illustrate the construction thereof.
Figure 5:
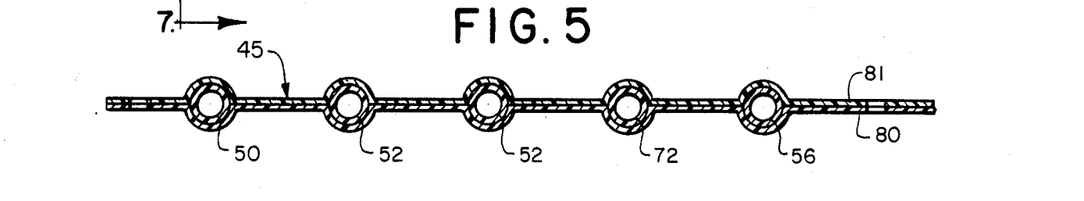
FIG. 5 is an enlarged cross-sectional view taken along line 5—5 of FIG. 4 showing in detail the construction of the fluid distribution manifold.

The system manifold 45 provides, in accordance with the invention, selective fluid communication between the eleven system fluid ports of the manifold. Referring to FIG. 4 the system manifold 45 is seen to be formed from two sheets 80 and 82 of plastic material bonded together by dielectric heating or other appropriate means along a peripheral seal line 82 (FIG. 4) to form within the manifold an interior chamber 83. To provide a fluid-sealed engagement with each of the connecting tubing segments the tubing segments are in a generally parallel-spaced arrangement extending through seal line 82 along one side of the manifold. As shown in FIG. 3, this allows the manifold to be readily inserted into actuator head 28 since all tubing segments extend from the non-inserted side. As shown in FIG. 5, the two fluid-impermeable plastic sheets 80 and 81 are actually sealed to the exterior of the tubing as it extends across the seal line, forming a permanent connection of high mechanical and fluid integrity.

Figure 6:
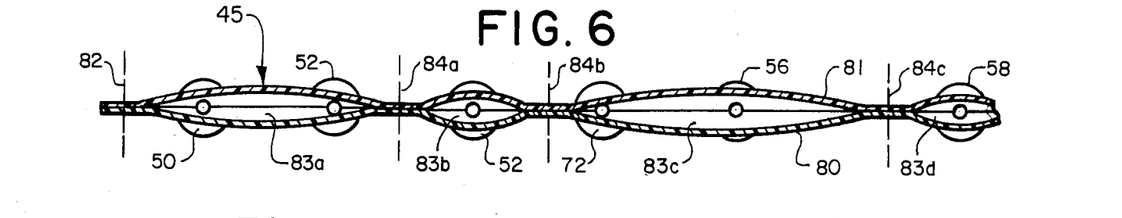
FIG. 6 is a cross-sectional view taken along line 6—6 of FIG. 5 showing further details of the construction of the the fluid distribution manifold.
Figure 7:
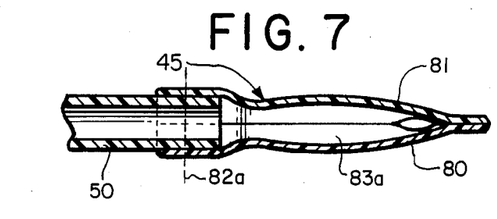
FIG. 7 is an enlarged cross-sectional view taken along line 7—7 of FIG. 4 showing further details of the fluid distribution manifold.
Figure 8:
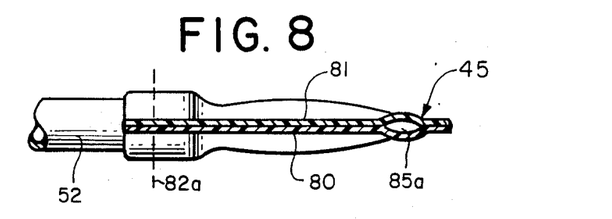
FIG. 8 is an enlarged cross sectional view taken along line 8—8 of FIG. 4 showing further details of the fluid distribution manifold.
Figure 9:
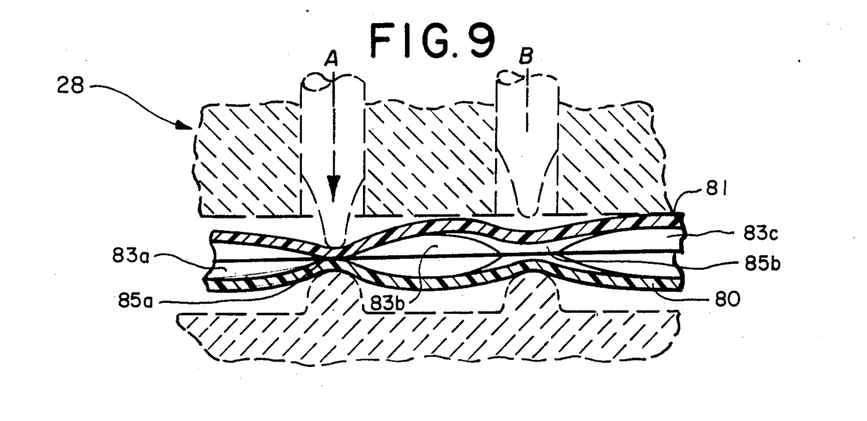
FIG. 9 is a cross-sectional view taken along line 9—9 of FIG. 4 showing the fluid distribution manifold installed in the actuator head of the apparatus and illustrating the operation of valving elements contained therin.

To provide for controlling fluid flow between the connecting tubing segments, manifold 45 includes, in accordance with one aspect of the invention, eight interior baffle portions 84a–84h formed by extending the seal line between sheets 80 and 81 from the seal line 82a extending through the tubing segments partially across chamber 83 toward seal line portion 82b. This has the effect of forming nine interior compartments 83a–83i within chamber 83, as shown in FIGS. 4 and 6. In addition, the interior baffles 84a–84h form eight valving passages 85a–85h between adjacent compartments within chamber 83. The valving passageways 85a–85h are normally open when manifold 45 is not installed in the control head 28 of appratus 21, allowing fluid flow between the tubing segment connecting with manifold 45. Since the seal line 82a extending along the connecting side of manifold 45 overlies each of the connecting tubing segments, as shown in FIGS. 7 and 8, the tubing segments are maintained in fluid-sealed communication with the associated compartments of chamber 83. Since seal line portion 82b extends only along the insert side of the manifold, passageways 85a–85h remain open in the absence of externally applied pressures, as shown in FIG. 8.

In accordance with the invention, fluid communication between compartments 83a–83i is controlled by selectively crimping closed required ones of valving passageways 85a–85h. To this end, fluid manifold 45 is inserted in a slot-shaped aperture 90 provided on the front surface of control head 28. The fluid manifold is inserted such that the insert side extends into the receptacle 90, and the connecting side faces in the opposite direction such that the tubing segments can freely connect to associated components of the system, as shown in FIG. 1. To insure accurate positioning within receptacle 90, the depth of the receptacle is made to correspond to the width of the manifold. In addition, a plurality of locating pins 91 may be provided along the lower front edge of the receptacle to engage alignment apertures 92 provided along the connecting side of the manifold. In practice, the manifold is sufficiently flexible to allow insertion into receptacle 90 over pins 91. Only after the manifold has been completely inserted with the valving side thereof against the rear wall of the receptacle is the connecting side lowered over the alignment pins.

Figure 10:
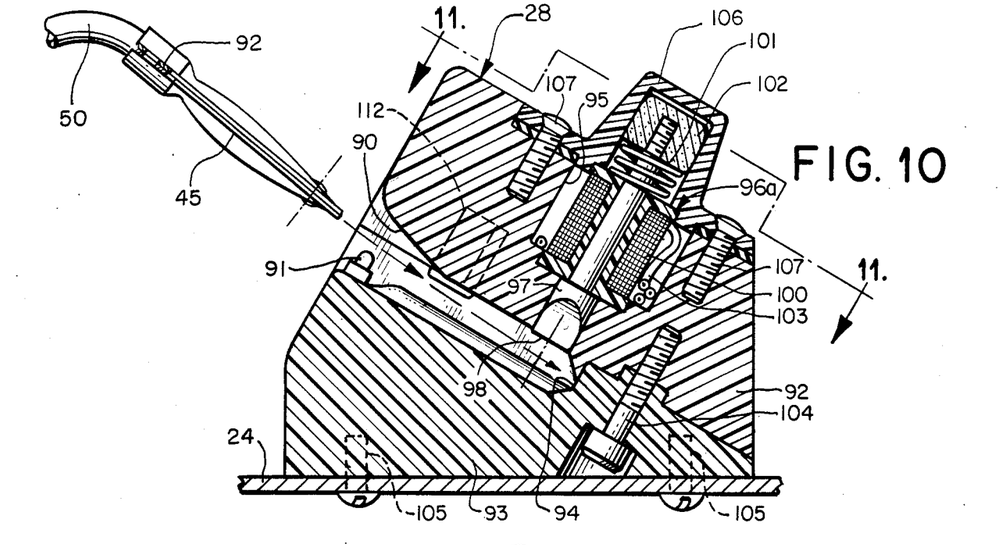
FIG. 10 is an enlarged cross-sectional view of the actuator head taken along line 10—10 of FIG. 3 showing a representative valving actuator element therein in a non-actuated state.

Referring to FIG. 10, the slot-shaped receptacle 90 is formed between two block-like actuator members 92 and 93. The slot-shaped receptacle 90 extends between the two blocks, terminating in a rear wall 94 which forms a back stop for the manifold when fully inserted, as shown in FIG. 12.

Figure 11:
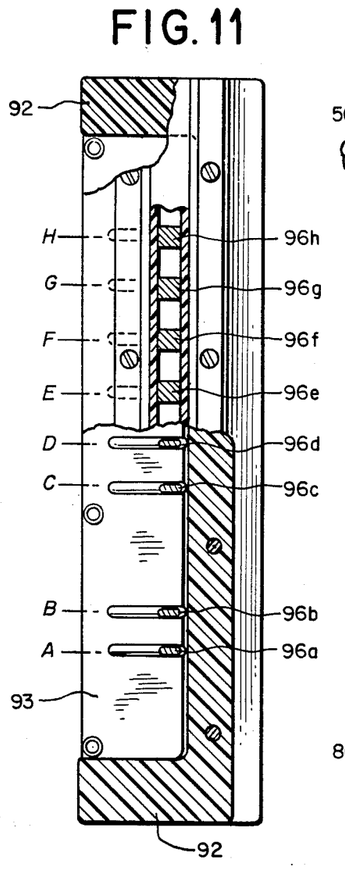
FIG. 11 is a top plan view partially in section of the actuator head showing the placement of the individual actuator elements therein.

Within a recess 95 in the upper head block 92 the flow control head 28 includes eight valve actuator assemblies 96a–96h. As shown in FIG. 11, these valve actuator assemblies are arranged in lateral alignment with respective ones of valving passages 85a–85h. Consequently, when manifold 45 is inserted in receptacle 90 with alignment pins 91 engaged, as shown in FIG. 12, the valve actuator assemblies overlie their respective valving passageways.

Each of the valve actuators includes a slidably-mounted plunger 97 which includes at one end a blade-like actuator surface 98. When the actuator assembly is energized, the plunger projects from a retracted position, as shown in FIG. 13a, to an extended position, as shown in FIG. 13b. The blade-like surface 98 then causes the underlying valving passage to be crimped shut, thereby isolating respective adjacent chambers in the manifold.

Figures 12, 13A, 13B:
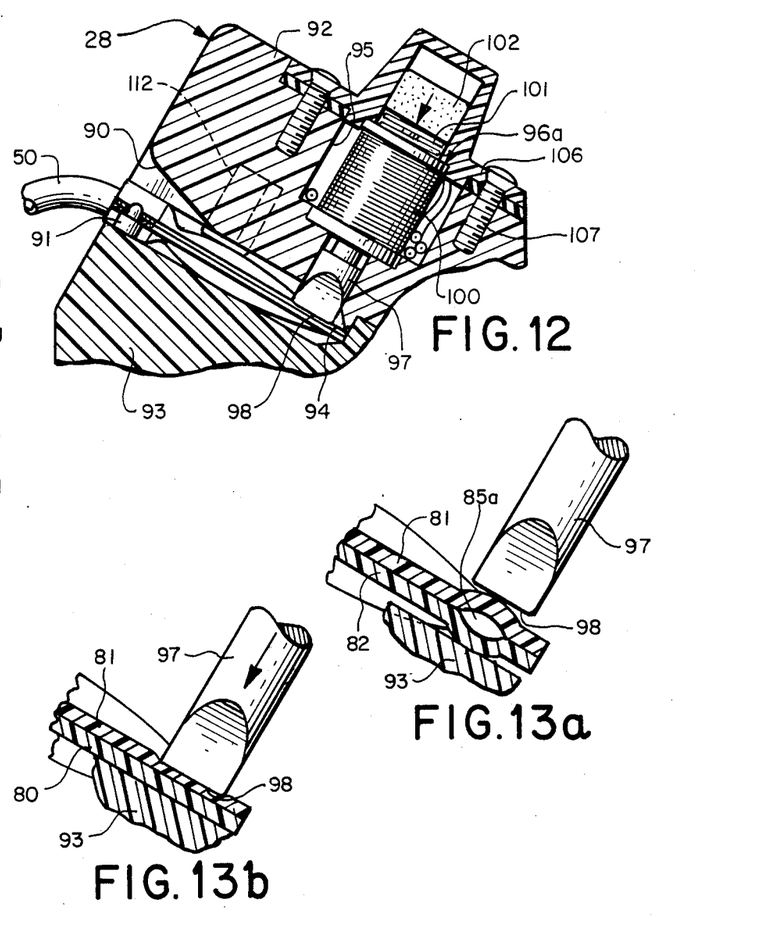
FIG. 12 is a partial cross-sectional view similar to FIG. 10 showing the valve actuator in an actuated condition.
FIG. 13a is an enlarged cross-sectional view of the actuator element and fluid distribution manifold with the valving passageway open.
FIG. 13b is a view similar to FIG. 13a showing the manifold passage actuated closed.

Actuation of plunger 97 to the crimping position shown in FIG. 12 is accomlished by energizing a solenoid 100 provided within each of the eight valve actuators 96a–96h. When the solenoid is not energized, the valve stem is biased free of receptacle slot 90 by a helical spring 101 provided above solenoid 100. An end cap 102 serves as an armature for solenoid 100. A plurality of electrical conductors 103 within recess 95 connect the solenoids of the valve actuators to appropriate actuating circuitry.

The two head blocks 92 and 93 may be held together by a plurality of machine screws 104. The bottom head block 93 may be attached to the top panel 24 of housing 23 by means of machine screws 105. A cover 106 overlying recess 95 may be attached to head block 92 by a plurality of machine screws 107.

To provide for actuation of valve actuators 96a–96h as required in performing a particular fluid processing procedure, the fluid processing system 20 of the present invention includes within processing apparatus 21 process control circuits 110 (FIG. 2). These circuits receive inputs from control panel 30 to actuate appropriate ones of the valve actuators as required in initiating and performing the procedure.

Also, in accordance with another aspect of the invention, fluid manifold 45 may be provided with a code strip 111 for providing data to process control circuits 110 indicative of selected characteristics of the installed fluid circuit 22. Specifically, code strip 111 may be provided along one edge of the manifold and may take the form of a plurality of apertures appropriately spaced and positioned to convey a desired code. The code may be automatically read upon insertion of the manifold into recess 90 by means of a reading station 112 located within the recess. In the case of the coded apertures, the reading station may contain a plurality of electrical brush contacts which extend through the apertures to complete an electrical circuit, thereby establishing the position of the apertures and the code to be conveyed. Alternately, an optical or magnetic coding strip may be provided. Also, the indicia may be provided at various locations on manifold 45, the only requirement being that the indicia be positioned in operative engagement with reading head 112 when the manifold is inserted in recess 90.

With the configuration described, the fluid processing system 20 can be utilized to perform multiple blood fractionation procedures. One such fractionation procedure is a batch processing procedure, wherein whole blood is drawn through a single-lumen needle, passed through a plasma-separation filter, and temporarily stored during an initial draw cycle. Then, during a subsequent return cycle, the processed whole blood is recirculated through the plasma separation filter and returned to the donor through the same single-lumen needle. Thus, in this procedure flow through the phlebotomy needle is bidirectional, and passes through the filter twice in the course of a complete cycle.

Figure 14:
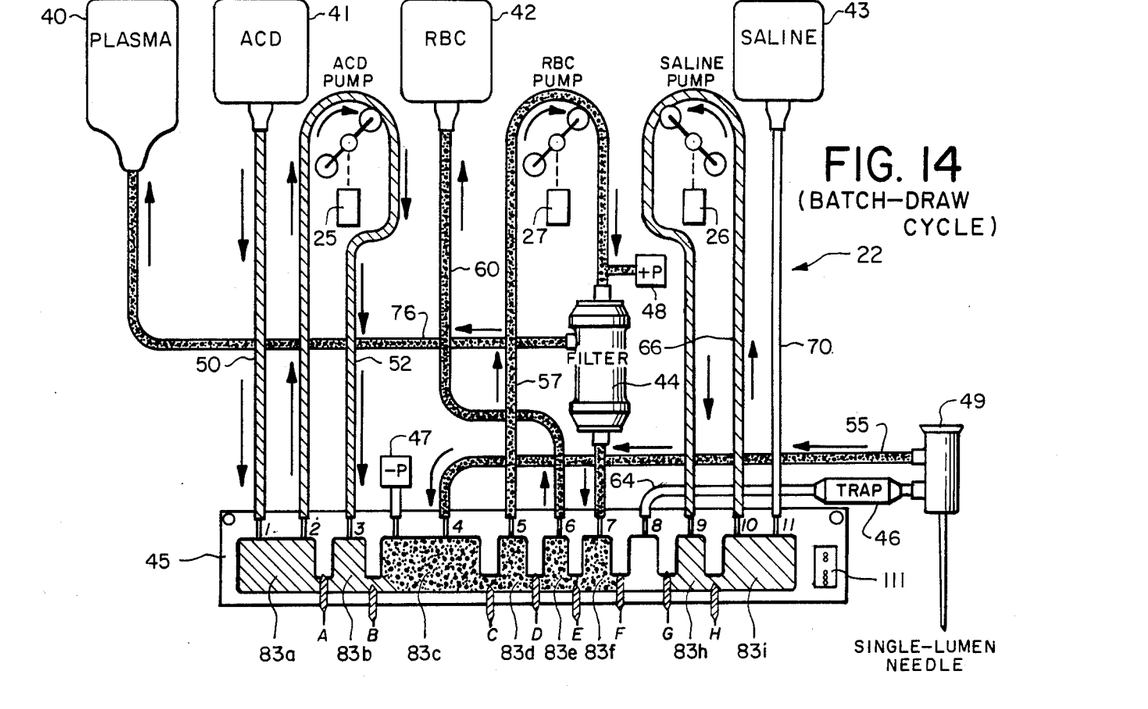
FIG. 14 is a simplified flow diagram of the blood fractionation system showing the system in the draw cycle portion of a batch flow procedure.

The fluid processing system of the present invention readily lends itself to this procedure. Referring to FIG. 14, during a draw cycle whole blood is derived through a single-lumen needle and conveyed by tubing segment 55 to manifold 45. In performing this process, processor control circuits 110 actuate valve actuators 96a, 96d, 96f and 96g. This allows anticoagulant fluid from ACD container 41 to be pumped through tubing segment 50, compartment 83a, tubing segment 52 and compartment 83b to compartment 83c, wherein it mixes with the acquired whole blood to prevent the coagulation in a manner well known to the art. Whole blood is advanced through compartment 83d and tubing segment 57 to the plasma separation filter 44 by RBC pump 27. Within filter 44, plasma is separated from the whole blood. The separated plasma is conveyed by tubing segment 76 to the plasma collection container 40. Plasma-deficient whole blood from filter 44 is conveyed through compartments 83f and 83e through tubing segment 60 to RBC container 42.

At this time saline is not required. However, the saline pump 26 continues to operate, circulating saline solution through tubing segment 66 and manifold chambers 83h and 83i. This recirculation maintains a continuous operating pressure within tubing segment 66 as it coacts with saline pump 26, thereby serving to maintain metering accuracy in the saline pump during subsequent introduction of saline into whole blood being processed in the system. Also, this allows double stringing of saline supply line 66 with the whole blood processing line 57 on RBC pump 27, if desired, to obviate the need for saline pump 26. This is in accordance with another aspect of the invention.

The collection of plasma-deficient red blood cells in container 42 continues until predetermined volume or weight of the cells has been collected. The collection of red blood cells in container 42 is typically monitored by means of a weight transducer 120 and associated circuitry, which provides an output signal indicative of the weight, and hence the volume, of the collected fluid. The output of this transducer circuit is applied to processor control circuits 110, wherein it causes the draw cycle to be terminated and a return cycle to be initiated.

Figure 15:
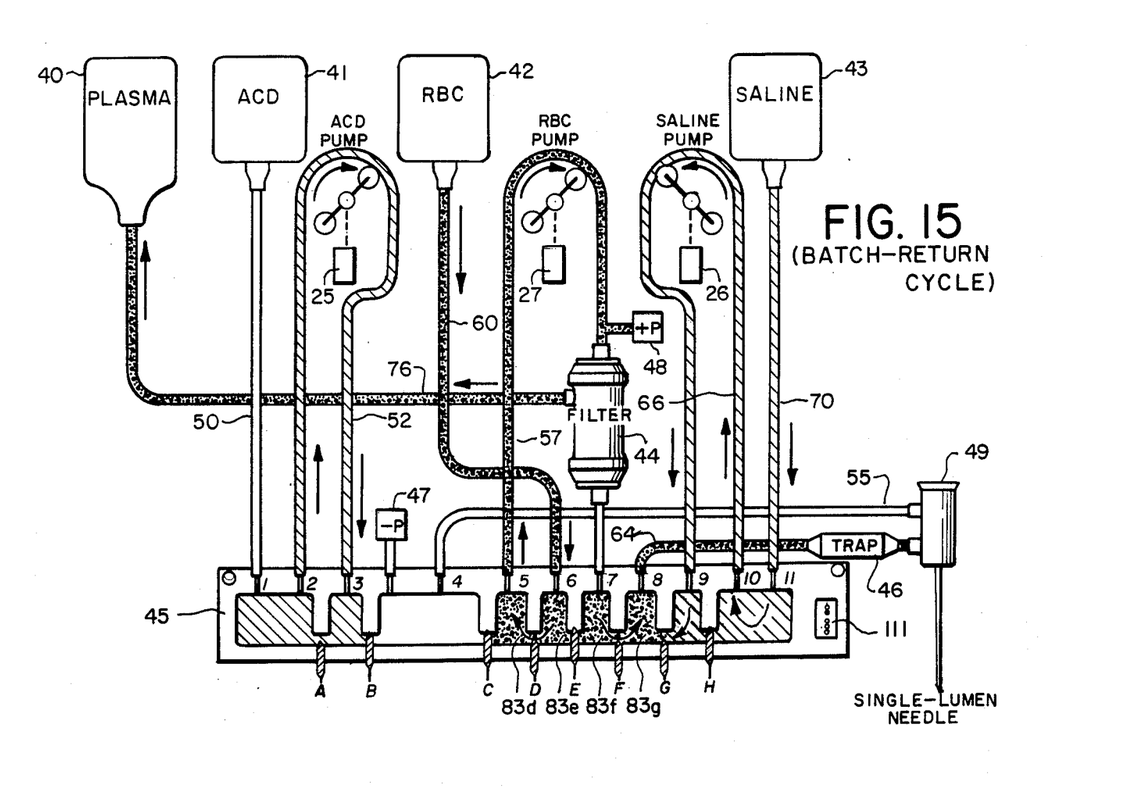
FIG. 15 is a flow diagram similar to FIG. 14 showing the system in the return cycle portion of a batch flow procedure.

Referring to FIG. 15, during the return cycle processor control circuits 110 cause valve actuators 96b, 96c, 96e and 96h to be actuated. With continued operation of pumps 25, 26 and 27, the plasma-deficient whole blood in container 42 is pumped through tubing segment 60, manifold compartment 83e, compartment 83d and tubing segment 57 to a plasma separation filter 44. With the second pass of plasma-deficient whole blood through filter 44, additional plasma is derived. This plasma is conveyed through tubing segment 76 to plasma collection container 40. The twice-filtered whole blood from filter 44 is conveyed through manifold compartments 83f and 83g and tubing segments 64 to the single lumen needle 49. Trap 46 operates in a conventional manner to detect bubbles or fluid absence in the return line 64.

The return cycle continues until the volume of fluid in RBC container 42 falls to a level which causes weight transducer 120 to cause processor control circuits 110 to terminate the return cycle and initiate another draw cycle. The system continues to operate with alternate draw and return cycles, each process quantity, or aliquot, being twice-passed through filter 44 for improved separation efficiency.

During the draw and return cycles pressure in the system may be continuously monitored by the negative pressure monitor 47 and positive pressure monitor 48. The negative pressure monitor 47 guards against collapse of a vein in the donor, and the positive pressure monitor 48 allows the fluid pressure in filter 44 to be set for maximum filter efficiency. The speeds of the ACD pump 25, the saline pump 26 and the RBC pump 27 may be adjusted in a known manner to maintain optimum system efficiency. Furthermore, where it is desired to use only two pumps, by reason of the closed-loop recirculation provided in the ACD supply line 50, it is possible to utilize a single pump for the ACD pump and RBC pump functions, tubing segments 52 and 62 then being double-strung on the single pump. During the return cycle saline may be added to the twice-processed whole blood through tubing segment 70 manifold chamber 83i and tubing segment 66 under the control of saline pump 26.

The fluid processing system of the present invention is also capable of performing a continuous flow procedure wherein whole blood is continuously withdrawn, processed and returned, either through two single-lumen needles or a single double-lumen needle. This procedure is often preferred, in that, because of its efficiency, it requires less time to process a given quantity of whole blood than the previously described batch procedure.

Figure 16:
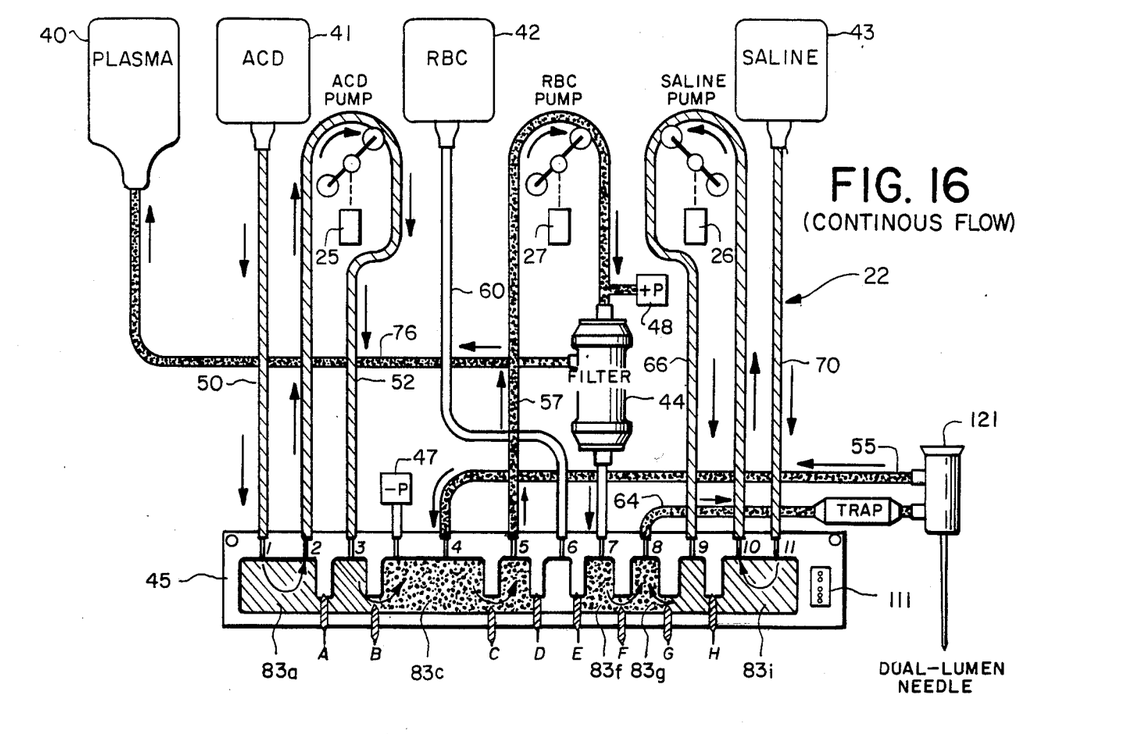
FIG. 16 is a simplified flow diagram showing the blood fractionation system during a continuous flow procedure.

Referring to FIG. 16, fluid circuit 22 is connected to a dual-lumen phlebotomy needle 121. Processor control circuits 110 actuate valve actuators 96a, 96d, 96e and 96h. Upon operation of pumps 25, 26 and 27 whole blood is withdrawn through one lumen needle 121 and conveyed through tubing segment 55 to manifold compartment 83c. At the same time, anticoagulant solution is pumped by ACD pump 25 through tubing segments 50 and 52 to compartment 83c to prevent coagulation. Whole blood is then pumped by RBC pump 27 through tubing segment 57 to filter 44, which functions in a conventional manner to remove plasma for storage in container 40. The plasma-deficient whole blood is then conveyed through manifold compartments 83f and 83g to tubing segment 64 for return to the donor through the other lumen of phlebotomy needle 121. The process is continuous, whole blood being continuously withdrawn from the donor, and plasma-deficient blood being continuously returned. Saline is added as required by saline pump 26, which pumps saline through tubing segments 70 and 66 to manifold compartment 83g.

In practice, the continuous flow procedure may continue until a predetermined quantity of plasma has been collected. The collection rate and volume can be monitored by means of a transducer 122 from which the plasma container is suspended. The output of this transducer, which may comprise an analog signal indicative of the weight of the container and collected fluid, is applied to the processor control circuits 110 to provide an indication to the user of the collected volume.

Figure 17:
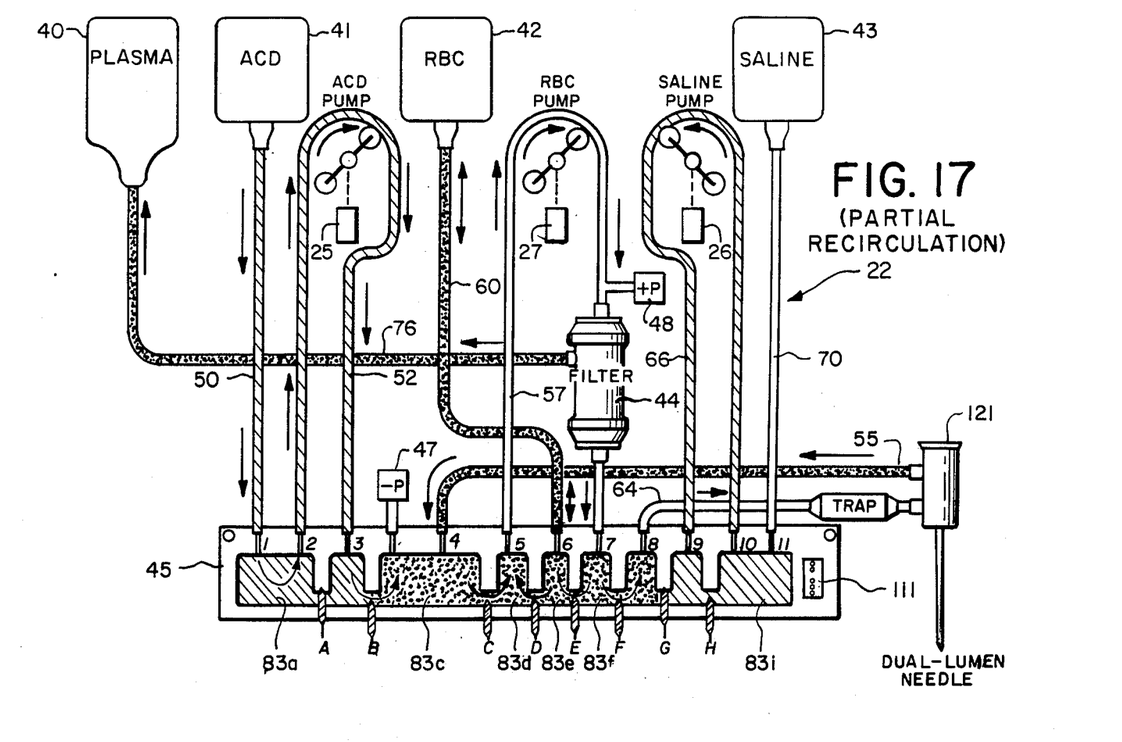
FIG. 17 is a simplified flow diagram showing the blood processing system during a partial recirculation procedure.

A processing system 20 of the invention may also be utilized to perform a partial recirculation procedure wherein a portion of plasma-deficient whole blood from plasma separation filter 44 is conveyed to container 40 for interim storage, and the remaining portion is returned to the donor through tubing segment 64. To accomplish this partial recirculation, the system is configured as for continuous flow in FIG. 16, except that valve actuators 96d and 96e are alternately released and actuated to allow a portion of the plasma-deficient whole blood from filter 44 to enter reservoir 42. When valve actuator 96e is released, allowing fluid flow between manifold compartments 83f and 83e, the plasma-deficient whole blood flows to containter 42. Then, when valve actuator 96f is actuated and actuator 96e is released, the once-processed whole blood flows from manifold compartment 83e to manifold compartment 83d, joining unprocessed whole blood withdrawn by phlebotomy needle 121. In this manner, the portion of the once-processed blood is reprocessed, increasing the efficiency of filter 44 over the single-pass arrangement of FIG. 16.

The various components of the fluid processing system, including containers 40-43, bubble trap 46 and plasma separation filter 44, may be conventional in construction and operation. In particular, the fluid absence detector 34 and associated bubble trap 46 of the fluid circuit may be similar in structure and operation to that described in U.S. Pat. No. 4,341,116 to Arnold C. Bilstad et al.

Container 42 and plasma container 40 are preferably hung at the same height to avoid the need for an equalizer valve at the whole blood and collected plasma outlets of filter 44. However, under some circumstances an equalizer valve may be provided to restrict the plasma outlet port until the pressure of the plasma in the filter reaches that of plasma-deficient blood flowing from the filter, and thereafter to modulate plasma flow through conduit segment 76 to maintain the pressure equivalence. A preferred construction for such an equalizer valve is described in the copending applications of Clinton Kopp et al, "Membrane Plasmapheresis Apparatus and Procedure", Ser. No. 277,428 filed June 25, 1981, now abandoned, continuation application Ser. No. 542,565 filed Oct. 19, 1983; "Fluid Flow Control Device", Ser. No. 277,449 filed June 25, 1981, now U.S. Pat. No. 4,412,553; and "Fluid Flow Control Device", Ser. No. 277,414, filed June 25, 1981, now U.S. Pat. No. 4,431,019; all assigned to the present assignee. A transmembrane pressure (TMP) monitoring system, such as described in the copending application of Arnold C. Bilstad et al., "Trans-Membrane Pressure Monitoring System", Ser. No. 403,362, filed June 30, 1982, now U.S. Pat. No. 4,493,693 may be provided in apparatus 21 to assist the user in making adjustments for maximum operating efficiency of filter 44.

One form of filter which is particularly attractive for use in the plasmapheresis applications illustrated herein utilizes a plurality of parallel microporous hollow fibers arranged side-by-side in the form of a bundle within a hollow cylinder. As whole blood is caused to flow through the fibers the plasma component passes through the walls of the fibers to the surrounding container, which forms a collections chamber from which the component is transported to a collection container. A preferred construction and method of manufacture of such a flow-through hollow fiber filter is shown in the copending application of Robert Lee and William J. Schnell, entitled, "Microporous Hollow Fiber Membrane Assembly and It Method of Manufacture", Ser. No. 278,913, filed June 29, 1981 now abandoned, continuation application Ser. No. 604,396 filed Apr. 26, 1984. A blood fractionation system providing recirculation is described in the copending application of Arnold C. Bilstad et al., entitled "Increased Yield Blood Component Collection System and Methods", Ser. No. 411,057, filed Aug. 24, 1982 now abandoned, continuation application Ser. No. 690,399 filed Jan. 9, 1985. A system for single-needle blood fractionation employing a single lumen phlebotomy needle is described in the copending application of Arnold C. Bilstad et al., entitled "Single Needle Blood Fractionation System Having Adjustable Recirculation Through Filter", Ser. No. 498,581, filed May 26, 1983, now allowed and assigned to the present assignee.

Thus, a novel fluid separation system has been shown and described which utilizes a unitary fluid flow control manifold which can be installed in an associated apparatus in a single installation step. Furthermore, the fluid manifold simplifies interconnections within the system, and allows a single fluid circuit construction to accommodate a multiple number of fluid procedures.

It will be appreciated that the fluid manifold of the invention can be utilized in conjunction with other types of fluid systems for performing other procedures.

While in the illustrated embodiment the two fluid impervious sheets forming the manifold are both formed of a flexible plastic material, for improved ease of installation, one of the fluid impervious sheets of the manifold can be constructed of relatively rigid material. Furthermore, the crimping functions within head 28 can be performed by means of pneumatic, hydraulic or cam-operated mechanical valve actuators, instead of the electrical solenoid actuators shown. Also, where it is desired to eliminate both the saline pump 26 and the ACD pump 25, the saline supply line 70 and the ACD supply line 50 can be triple strung on RBC pump 27, valving passages 85g and 85h, and 85a and 85b being crimped shut and released open as required to control the introduction of saline and ACD into the system.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

We claim:

1. A fluid processing system comprising a fluid circuit including
    a plurality of tubing segments each having an end portion, and
    a fluid distribtuion manifold integrally attached in flow communication with each of said tubing segments, said manifold including
    a pair of fluid impermeable sheets having opposite side edges peripherally sealed together to define a manifold interior,
    means for sealingly engaging said end portion of each of said tubing segments in a parallel spaced relationship along one of said sealed side edges, so that said tubing segments all communicate with said manifold interior, and
    means for defining a plurality of baffles extending within said manifold interior between adjacent, sealingly engaged tubing segment end portions, said baffles extending from said one sealed side edge toward the opposite one of said sealed side edges to compartmentalize said manifold interior into adjacent fluid chambers, each associated with at least one of said flexible tubing segments, said baffles each having an end located at a generally equal distance from said opposite sealed side edge to define between said baffle ends and said opposite sealed side edge a plurality of mutually aligned passageways normally opening fluid communication between said adjacent fluid chambers and, thus, between associated tubing segments, and
    a processing apparatus including
    a receptacle for releasably receiving said opposite sealed side edge of said manifold with said tubing segments extending from said one sealed side edge externally of said receptacle,
    pumping means attachable to at least one of said externally extending tubing segments to pump fluid through said fluid circuit,
    a plurality of valve actuator assemblies located within said receptacle, each of said valve actuator assemblies being aligned with one of said mutually aligned manifold passageways and being operative for selectively closing said aligned passageway to block fluid communication between the adjacent fluid chambers, and
    process control means for actuating each of said valve actuator assemblies in a predetermined pattern to control fluid flow between fluid chambers within said manifold, thereby controlling fluid flow through said fluid circuit to achieve a desired fluid processing procedure,
    said fluid manifold further including indicia thereon indicative of the procedure, said control means being responsive to said indicia.

2. A fluid flow system as defined in claim 1 wherein said sheets are formed of plastic material.

3. A fluid flow system as defined in claim 1 wherein one of said sheets is relatively rigid.

4. A fluid flow system as defined in claim 1 wherein said manifold is generally rectangular in form.

5. Processing apparatus as defined in claim 1 wherein said valve actuators comprise electrically actuated solenoids.

6. Processing apparatus as defined in claim 1 wherein said receptacle includes index means for locking the fluid manifold in position relative to the valve actuator.

7. Processing apparatus as defined in claim 1 wherein said indicia comprise a plurality of apertures in the manifold, and said control means include electrical recognition means responsive to said apertures.

* * * * *